United States Patent [19]

Zimmerman et al.

[11] 4,001,247

[45] Jan. 4, 1977

[54] 1-ETHYL 3A-(SUBSTITUTED-PHENYL) DECAHYDROISOQUINOLINE

[75] Inventors: Dennis M. Zimmerman, Indianapolis; Winston S. Marshall, Bargersville, both of Ind.

[73] Assignee: Eli Lilly and Company, Indianapolis, Ind.

[22] Filed: June 7, 1974

[21] Appl. No.: 477,220

[52] U.S. Cl. .................. 260/289 D; 260/287 D; 424/258
[51] Int. Cl.² ..................................... C07D 217/12
[58] Field of Search ........ 260/289 D, 289 R, 287 D

[56] References Cited

FOREIGN PATENTS OR APPLICATIONS 802,557   11/1973   Belgium ..................... 260/289

*Primary Examiner*—Raymond V. Rush
*Assistant Examiner*—D. B. Springer
*Attorney, Agent, or Firm*—James L. Rowe; Everet F. Smith

[57] ABSTRACT

1-Ethyl-3a-substituted-phenyl decahydroisoquinolines, useful as an analgetic agonist and analgetic antagonist.

6 Claims, No Drawings

1-ETHYL 3A-(SUBSTITUTED-PHENYL) DECAHYDROISOQUINOLINE

BACKGROUND OF THE INVENTION

It has long been known that slight chemical modifications of the morphine molecule lead to analgesic agonists of widely differing potency and addictive properties. For example, codeine, the methyl ether of morphine, is a relatively mild analgesic agonist having slight dependance (addiction) liability. On the other hand, heroin, the diacetyl derivative of morphine, is a powerful agonist with extremely high addiction potential. In addition, as long ago as 1915, Pohl found that when the N-methyl group of codeine was replaced with an allyl group, the resulting compound, N-allylnorcodeine, was an opiate antagonist. In 1940, N-allylnormorphine or nalorphine was synthesized and was shown to have a highly specific ability to reverse the depressant effects of morphine. Other simple chemical modifications of the morphine molecule have yielded many interesting drugs. Thus, one fruitful research area in the search for improved analgesics of high potency and/or lower dependence (addiction) liability has been the chemical modification of the morphine molecule.

In addition to modifying the morphine ring structure by chemical means, chemists have developed a second related field of research—the preparation of certain morphine part-structures—with the same end in mind as above; i.e., the synthesis of improved analgesic agonists and/or analgensic antagonists of improved properties. For example, meperidine, a widely used analgesic, can be written as a morphine part-structure. Many other morphine part-structures have been prepared, some of which have improved analgesic agonist properties and others, particularly those with an allyl group attached to a ring nitrogen, have opiate antagonist properties. It had been hoped that morphine part-structure research would produce a compound having both opiate agonist and antagonist properties since the opiate antagonist property would assure a user that the compound would have a greatly reduced dependence liability. Two recently marketed analgesics, pentazocine and phenazocine, have been found to be both antagonists and agonists although they still retain a certain degree of opiate dependance liability.

One potential morphine part-structure can be written as a decahydroisoquinoline with an hydroxyphenyl group substituted on a ring junction carbon atom para to the isoquinoline nitrogen. An attempt to prepare such a compound was described by Boekelheide in a paper appearing in J. Am. Chem. Soc., 69, 790 (1947). This paper set forth the preparation of what, according to the numbering system then in vogue, were 10-phenyldecahydroisoquinolines. It was the author's conclusion, however, that the compound (IX) had a cis configuration and (footnote 5) showed low analgesic activity. The synthesis itself is cumbersome and not free from ambiguity. Sugimotp et. al., J. Pharm. Soc. Japan, 75 177 (1955), C.A. 1956 1814b described the synthesis of 8 or 10-alkylated decahydroquinolines. The reference also shows the morphine part-structure, 10-(m-hydroxyphenyl)-3-methylisoquinoline [presently named as 1-methyl-3a-(m-hydroxyphenyl)-1,2,3,3a,4,5,6,7,7a,8-decahydroisoquinoline] but without furnishing a synthesis for it. These authors do not, in fact, describe the preparation of any decahydroisoquinoline, but describe only the preparation of the decahydroquinoline analogs.

Belgian Pat. No. 802,557 issued Jan. 19, 1974, discloses a general method of preparing N-substituted 3a-phenyldecahydroisoquinolines and specifically discloses 3a, phenyl-3a-(m-methoxy phenyl) and 3a-(m-hydroxyphenyl)-1-methyldecahydroisoquinolines, 3a-(m-methyoxyphenyl) and 3a-(m-hydroxyphenyl)-1-phenethyldecahydroisoquinolines. and 1-cyclohexylmethyl-3a-phenyldecahydroisoquinoline.

SUMMARY OF THE INVENTION

This invention provides decahydroisoquinolines of Structure 1 below:

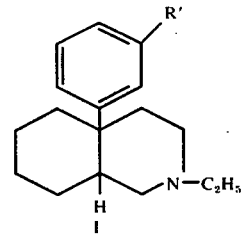

wherein
R¹ is O-alk, OH, or

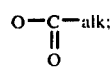

and
alk is (C₁–C₃) alkyl.

A preferred group of compounds of this invention are those in which R' is O-alk or OH and a particularly preferred group are those in which R' is OH only. Also included within the scope of this invention are the pharmaceutically-acceptable acid addition salts of the above bases formed with non-toxic acids. In the above formula, the term (C₁–C₃) alk, for which alk is the symbol, includes methyl, ethyl, isopropyl and n-propyl; thus, the term O-alk includes methoxy, ethoxy and the like. Similarly,

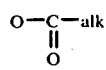

includes acetoxy, propionoxy and butyroxy.

The pharmaceutically acceptable salts of the amine bases of this invention represented by the above formula are formed with non-toxic acids, as for example, salts derived from inorganic acids such as: hydrochloric acid, nitric acid, phosphoric acid, sulfuric acid, hydrobromic acid, hydriodic acid, nitrous acid, phosphorous acid and the like, as well as salts derived from non-toxic organic acids including aliphatic mono and dicarboxylic acids, phenyl-substituted alkanoic acids, hydroxy alkanoic and alkandioic acids, aromatic acids, aliphatic and aromatic sulfonic acids, etc. Such pharmaceutically-acceptable salts thus include sulfate, pyrosulfate, bisulfate, sulfite, bisulfite, nitrate, phosphate, monhydrogenphosphate, dihydrogenphosphate, metaphosphate, pyrophosphate, chloride, bromide, iodide, fluoride, acetate, propionate, decanoate, caprylate, acrylate, formate, isobutyrate, caprate, heptanoate, propiolate, oxalate, malonate, succinate, suberate, sebacate, fumarate, maleate, mandelate, butyne-1,4-dioate, hexyne-1,6-dioate, benzoate, chlorobenzoate, methylbenzoate, dinitrobenzoate, hydroxybenzoate, methoxybenzoate, phthalate, terephthalate, bezenesulfonates, toluenesulfonate, chlorobenzenesulfonate, xylenesulfonate, phenylacetate, phenylpropionate, phenylbutyrate, citrate, lactate, β-hydroxybutyrate, glycollate, malate, tartrate, methanesulfonate propanesulfonate, naphthalene-1-sulfonate, naphthalene-2-sulfonate and the like salts.

The bridgehead substituents, the meta-substituted phenyl at 3a and the hydrogen at 7a, can have either a cis or trans relationship to one another; i.e., the two substituents can be on the same "side" of the decahydroisoquinoline ring system (cis) or on the opposite "side" (trans). In addition, both the 3a and 7a carbon atoms are asymmetric, thus giving rise in each compound to 4 optical isomers, occurring as two racemates designated as the cis-dl and the trans-dl-pair. Structure I is thus intended to comprehend both the optical isomers, the cis-dl and trans-dl racemates, and their individual enantiomorphs and the structural isomers since, as far as is known, all of the individual isomers and isomer mixtures are useful as analgesic agonists or as analgesic antagonists; albeit large quantitative differences in analgesic agonist or antagonistic potency may exist between individual isomers or racemates. We prefer, however, those compounds according to structure I above which are in the trans configuration; i.e., the trans-dl racemic pair and the individual trans isomers such as the trans-l compounds.

The compounds of this invention are prepared according to the following procedure using the synthesis of compounds in which R' is methoxyl for purely exemplary purposes:

2-(2-Cyanoethyl)-2-(m-methoxyphenyl) cyclohexanone, prepared by the method of Boekelheide, *J. Am. Chem. Soc.*, 69, 790 (1947), is hydrolysed to 2-(2-carboxyethyl)-2-(m-methoxyphenyl) cyclohexanone. The free acid thus formed is reacted with ethyl chloroformate in the presence of triethylamine which product is in turn reacted with sodium azide. The product of this reaction, an acyl azide, is decomposed under conditions which promote the Curtius rearrangement to yield an isocyanate which, upon refluxing with aqueous acid, yields an imine of Structure III, This reaction sequence is illustrated below:

Reaction Sequence 1

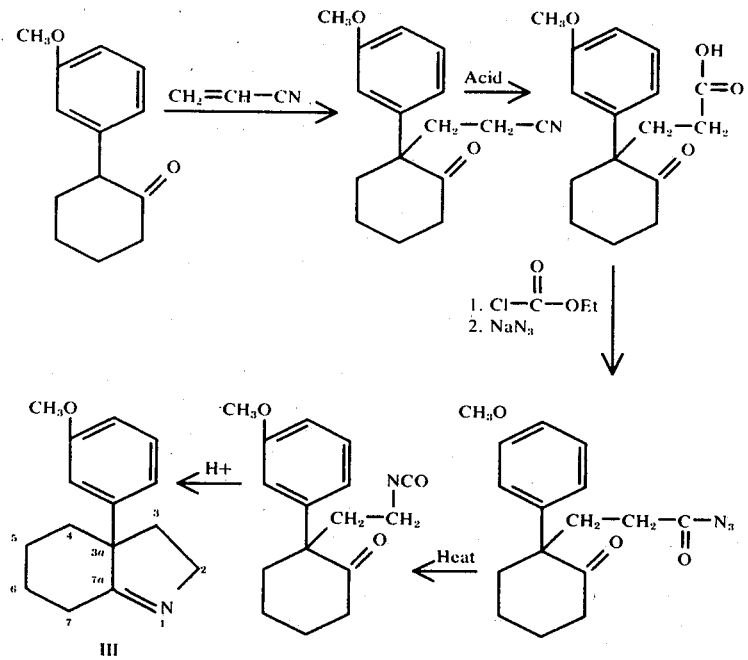

In carrying out the chemical transformations delineated in Reaction Sequence 1, we prefer to hydrolyze the nitrile function of 2-(β-cyanoethyl)-2-(m-methoxyphenyl)-cyclohexanone using a mineral acid in a strongly acidic medium; for example, 12N aqueous hydrochloric acid in 60–70 percent aqueous acetic acid. Other mineral acids such as sulfuric and phosphoric may also be used, as can a purely aqueous reaction medium, without affecting the yield or purity of the product in any way. Alkaline hydrolysis may also be used, but it is necessary to use somewhat more stringent reaction conditions in order to carry the hydrolysis past the intermediate amide stage to the salt of the free acid. Higher boiling inert solvents such as diethyleneglycol can be used. The second step of the reaction sequence, the formation of an acid chloride from the carboxylic acid of the previous step, can be accomplished by use of any of the milder chlorinating agents, for example, oxalyl chloride, thionyl chloride and the like. We prefer to use ethyl chloroformate. An acid acceptor such as triethylamine can also be used to advantage in forming the desired acid chloride, using an inert solvent. The reaction of the thus formed acid chloride with sodium azide to form the acid azide is carried out under standard conditions. It should be recognized, however, that an alternate procedure for preparing the azide exists; i.e., the formation of the hydrazide by reaction of anhydrous hydrazine with the acid chloride followed by azide formation with nitrous acid. Rearrangement of the azide under Curtius rearrangement conditions, consisting simply in heating the azide, however synthesized, at the reflux temperature of benzene or toluene for from 1 to about 24 hours, yields the expected isocyanate. Acidification of the isocyanate product yields directly a 3H-indole (III). The acidification is carried out by heating the isocyanate with a concentrated mineral acid as for example hydrochloric or sulfuric acid for from 12–24 hours. The product, as the free base, is isolated by basifying the acid reaction medium with, for example, sodium hydroxide, sodium carbonate or the like.

Structure III above is named 3a-(m-methoxyphenyl)-3H-indole or 3a-(m-methoxyphenyl)-3H-benzo[b]pyrrole and was prepared by Langlois et al. *Tetrahedron*, 27, 6541 (1971) using a different method of synthesis.

Reaction Sequence 2 below outlines the production of the compounds of this invention represented by Structure I, from the intermediates of Reaction Sequence 1. The 3H-indole (III) end product of Reaction Sequence 1 is methylated quantitatively to yield an iminium salt (IIIa) which compound is next reacted, also quantitatively, with diazomethane to yield an aziridinium salt (IV.) The aziridinium salt rearranges to produce a mixture of double-bond isomers (Va and Vb). Reduction of the enamine isomer (Va) with sodium borohydride in acetic acid yields a decahydroisoquinoline-VI or VIa-(I above in which R' is methoxy).

The trans-dl-racemate, (VI), is the predominant racemate isolated from this reaction with only minor quantities of the cis-dl-racemate (VIa) being found. Platinum hydrogenation also yields predominantly the trans-dl-racemate. On the other hand, hydrogenation of the enamine (Va) with 5 percent palladiumon-carbon yields a mixture of the cis-dl- and trans-dl racemates (40–60), which racemates are readily separated from each other by precipitating the trans-dl racemate as a picrate salt. The cis-dl racemate does not form an insoluble picrate. The above series of reactions is illustrated below in Reaction Sequence 2:

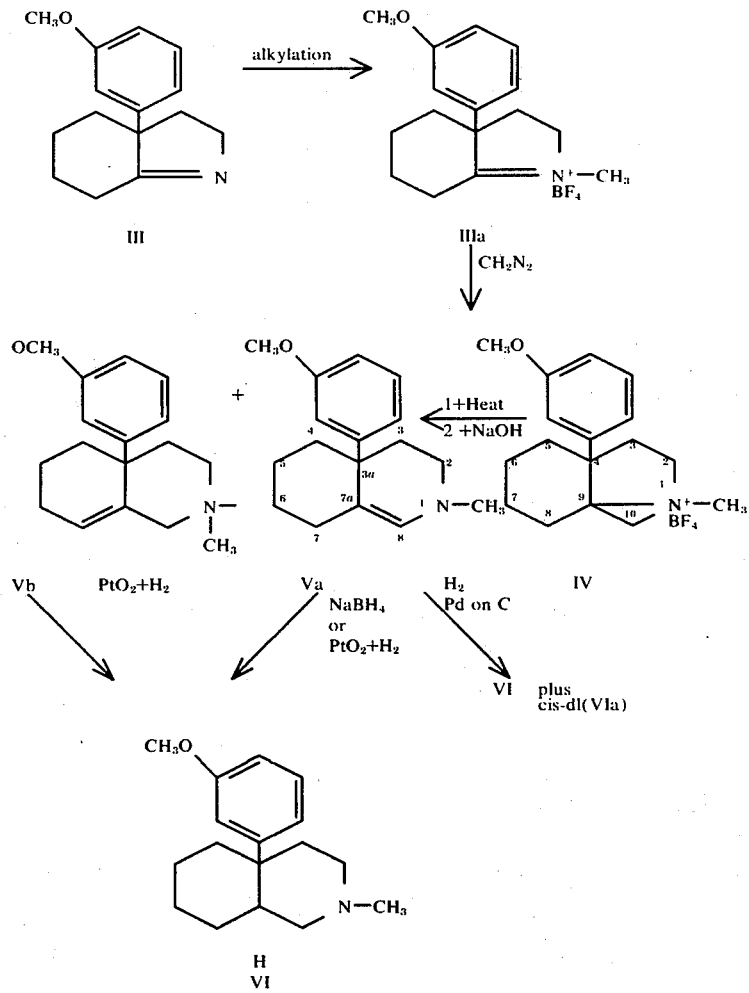

In carrying out the procedures outlined in Reaction Sequence 2 above, alkylation of the 3H-indole (III) to yield the quaternary methyl derivative (IIIa) is carried out preferably by treating the indole with trimethyloxonium tetrafluoroborate. Other alkylating agents can, however, be used as for example diemthyl sulfate, methyl iodide and the like. The product of this methylation reaction, an iodide or sulfate salt, is then metathesized to the fluoroborate salt by reaction with fluoroboric acid. Transformation of this quaternary salt to an aziridinium salt (IV) named systematically as a salt of 1-azonia-1-methyl-4-phenyl (or meta-substituted phenyl)tricyclo [4,2,1,0$^{1-9}$] decane), is accomplished by reacting the iminium salt with diazomethane. The diazomethane can be generated in situ or added as a solution in accordance with procedures long established in the art. The aziridinium salt is rearranged to yield a mixture of double-bond isomers (Va and Vb) (85–15) by heating, preferably for about 1 hour at about 200° C. although longer reaction times at somewhat lower temperatures will give essentially the same yields. The direct product of the rearrangement is an amine salt which must be treated with a base such as sodium hydroxide or sodium carbonate in order to provide the thus produced N-methyl octahydroisoquinolines (Va and Vb) as free bases. The reduction of the (Va and Vb) to the corresponding decahydroisoquinolines (VI and VIa) has been discussed above.

Compounds according to structure VI or VIa containing a meta-hydroxyphenyl substituent at C-3a are prepared from the corresponding methoxy compound by dealkylation using, for example, hydrobromic acid in acetic acid.

Compounds according to structure VI or VIa containing a meta-hydroxyphenyl substituent at C-3a are prepared from the corresponding compounds in which R' is methoxy (or another alkoxy group) by dealkylation using, for example, hydrobromic acid in acetic acid.

The preparation of compounds according to Formula I can be accomplished by several procedures. For example, the N-methyl derivative of VI in which R' can be either OH or O-alk above can be reacted with phenyl-chloroformate to yield a carbamate. Hydrolysis of this carbamate provides the secondary amine (I with H for C$_2$H$_5$). Alkylation of the secondary amine by standard procedures using ethyl bromide, ethyl iodide, diethyl sulfate or the like readily yields the compounds of this invention according to I above. Alternatively, an amide can be formed with the secondary amine function by reaction with acetyl chloride or acetic anhydride, and the amide reduced to a tertiary amine function with LiAlH$_4$ or other similar reducing agent, to yield compounds according to I.

In such acylations, R' should remain alkoxyl (other than hydrogen) until the amide is reduced to a tertiary amine function. Then the alkoxyl group can be cleaved by HBr to yield a compound according to I wherein R' is hydroxyl.

Again alternatively, the 3H-indole (III) in Reaction Sequence 2 can be alkylated to form an isomeric derivative in which the double bond migrates to the phenyl ring of the indole from the pyrrol ring (from the 7a-1 position to the 7-7a position). Any of the above ethylating agents can be employed in this procedure to give an N-ethyl derivative. The reaction of this new unsaturated 3H-pyrrole with HBF$_4$ yields again a cyclic iminium salt in which an ethyl group is attached to the indole nitrogen. This iminium salt can then be subjected to the previously exemplified diazomethane alkylation to yield an aziridinium derivative (similar to IV). Rearrangement followed by reduction then yields compounds according to VI and VIa in which the N-methyl group is replaced with N-ethyl.

Compounds according to I above in which R' is O-alk, alk being other than methyl, can be prepared either by employing as a starting material a 2-(2-cyanoethyl)2-(m-alkoxyphenyl) cyclohexanone in which the alkoxy group is ethoxy or propoxy, or can be derived from the m-hydrophenyl derivative by any standard phenolic ether synthesis.

Compounds according to I above in which R' is

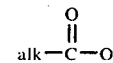

are prepared by standard acylation procedures from the corresponding compound in which R' is OH, such acylation procedures involving, for example, the reaction of an anhydride

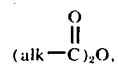

a mixed anhydride,

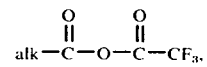

or an acid chloride

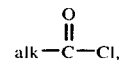

with the phenol or preferably, an alkali metal salt thereof.

This invention is further illustrated by the following specific examples.

EXAMPLE 1

A mixture was prepared containing 368 g. of 2-(β-cyanoethyl)-2-(m-methoxyphenyl)cyclohexanone, 2000 ml. of glacial acetic acid, 850 ml. of 12 N aqueous hydrochloric acid and 850 ml. of water. The mixture was refluxed for about 19 hours and then cooled to room temperature. Sufficient ice and water were added to make a volume of about 11 liters. The resulting mixture was stirred for about 30 minutes at which point a precipitate comprising 2-(β-carboxyethyl)-2-(m-methoxyphenyl)cyclohexanone formed. The supernate was removed by centrifugation, and the precipitate collected. The precipitate was thoroughly washed with water and then dried to yield about 280 g. of 2-(β-carboxyethyl)-2-(m-methoxyphenyl)cyclohexanone melting at about 143–4° C. after recrystallization from water.

About 225 g. of 2-(β-carboxyethyl)-2-(m-methoxyphenyl)cyclohexanone were mixed with 125 g. of triethylamine and about 20 g. of sodium sulfate. A solution of 99 g. of ethyl chloroformate in 3250 ml. of anhydrous ether was added in dropwise fashion. The reaction mixture was stirred for about 1 hour at about 0° C. at which point 89 g. of sodium azide in 350 ml. of water were added in dropwise fashion. After the addition had been completed, the reaction mixture was stirred for an additional two hours at 0° C. The organic layer was separated. 2-(β-Azidoformylethyl)-2-(m-methoxyphenyl)cyclohexanone formed in the above reaction was isolated as an oil by evaporation of the ether in vacuo. The residual oil was dissolved in 3.5 l. of benzene, and the solution heated at refluxing temperature for about 1.5 hours. The benzene was removed by evaporation in vacuo. By this procedure the azidoformyl group was rearranged under Curtius conditions to yield the corresponding isocyanate. The benzene was removed by evaporation in vacuo. The residual isocyanate was next hydrolyzed to the cyclic imine by heating overnight in a mixture containing 1200 ml. of water, 1200 ml. of glacial acetic acid and 1200 ml. of 12N aqueous hydrochloric acid. The hydrolysis mixture was cooled and then made strongly basic with 50 percent aqueous sodium hydroxide. 3a-(m-methoxyphenyl-2,3,3a,4,5,6,7-heptahydroindole thus produced was extracted into ether, and the ether layer separated, washed with water and dried. Evaporation of the ether layer to dryness yielded 153.2 g. of 3a-(-m-methoxyphenyl)-2,3,3a,4,5,6,7-heptahydroindole, distilling at about 140° C. at 0.07 mm/g. (For comparison, see Langlois et al., *Tetrahedron*, 27, 5641 (1971) compound 10 and page 5647, table 4, compound 42).

About 341 g. of 3a-(m-methoxyphenyl)-2,3,3a,4,5,6,7-heptahydroindole were dissolved in 600 ml. of methyl ethyl ketone. 184 g. of dimethyl sulfate were added to this solution in dropwise fashion. The reaction mixture was heated at refluxing temperature for 1 hour. 1100 ml. of water were then added over a one-half hour period and the reaction mixture refluxed for another 3 hours. The reaction mixture was made strongly basic with 50 percent aqueous sodium hydroxide with external cooling provided. 1-Methyl-3a-(m-methoxyphenyl)-1,2,3,3a,4,5,6-heptahydroindole formed in the above reaction, being insoluble in the alkaline layer, separated and was extracted into ether. The ether extract was separated, washed with water and dried. Evaporation of the ether in vacuo left a residual oil comprising 1-methyl-3a-(m-methyoxyphenyl)-1,2,3,3a,4,5,6-heptahydroindole boiling at about 144° C. at 0.4 mm/Hg; yield = 325.4 g.

325.4 g. of 1-methyl-3a-(m-methoxyphenyl)-1,2,3,3a,4,5,6-heptahydroindole were dissolved in 2500 ml. of ether. A 50 percent mixture of 50 percent fluoboric acid and anhydrous ethanol was added in dropwise fashion with stirring until the solution was acid to congo red. The ether layer was separated by syphoning. The aqueous layer which contained 1-methyl-3a-(m-methoxyphenyl)-2,3,3a,4,5,6,7-heptahydroindolinium fluoborate formed in the above reaction was allowed to stand while the fluoborate salt slowly crystallized. The salt was collected by filtration, and the filter cake washed with ether. The filter cake was then triturated with an anhydrous ethanol-ether solvent mixture. The solvent was separated by filtration, and the filter cake was dried. Yield of the fluoroborate salt was about 392 g.

A solution of 55 g. of 1-methyl-3a-(m-methoxyphenyl)-2,3,3a,4,5,6,7-heptahydroindolinium fluoborate in 500 ml. of methylene chloride was cooled to about 0° C. A solution of diazomethane prepared from 103 g. of N-methyl-N-nitroso-p-toluenesulfonamide in ether was added over a five-hour period. The reaction mixture was allowed to warm to room temperature and was stirred overnight. The supernate was separated from the precipitated oil comprising the fluoboroate salt of the corresponding aziridinium compound, 1-azonia-1-methyl-4-(m-methoxyphenyl)tricyclo[4,2,1,0²⁻⁸ᵃ] decane. The oily residue was triturated with three 1000 ml. portions of ether, and the ether washes were discarded. The residual oil was transferred to a 500 ml. round-bottom flask and heated at atmospheric pressure for about one hour at 200° C., thus forming 1-methyl-3a-(m-methoxyphenyl)-1,2,3,3a,4,5,6,7-octahydroisoquinoline, which compound was dissolved in anhydrous ethanol, and the ethanol solution treated with an excess of 50 percent aqueous sodium hydroxide and water. The octahydroisoquinoline, being insoluble in the alkaline solution, separated and was extracted into ether. The ether extract was separated and dried, and the ether removed therefrom by evaporation in vacuo. 1-methyl-3a-(m-methoxyphenyl)-1,2,3,3a,4,5,6,7-octahydroisoquinoline thus prepared distilled at about 168° C. at 0.5 mm/hg.

A mixture was prepared containing about 163 g. of 1-methyl-3a-(m-methoxyphenyl)-1,2,3,3a,4,5,6,7-octahydroisoquinoline, 90 g. of sodium borohydride and 4500 ml. of tetrahydrofuran was cooled to about 5° C. 1630 ml. of acetic acid were added in dropwise fashion while maintaining the temperature below about 10° C. The mixture was stirred for one-half hour at about 5° C. and the gradually warmed to refluxing temperature with mild heating. The mixture was refluxed for 1 hour, and was then made strongly basic with about 3 liters of 25 percent aqueous sodium hydroxide. The tetrahydrofuran layer was decanted, and the aqueous layer washed with three 2-liter portions of ether. The ether and tetrahydrofuran layers were combined and evaporated to dryness in vacuo. The resulting residue, comprising 1-methyl-3a-(m-methoxyphenyl)-1,2,3,3a,4,5,6,7,7a,8-decahydroisoquinoline formed in the above reaction was dissolved in about 3.5 l of ether, and the ethereal layer washed with three 2 l. portions of water. The ether layer was dried, and the ether removed therefrom by evaporation to dryness in vacuo. The yield of the decahydroisoquinoline was 162.3g.

The compound was purified via the picrate salt which was converted back to the free base by refluxing the salt with saturated lithium hydroxide at the ratio 30 g. of picrate to 1000 ml. of saturated aqueous lithium hydroxide solution. Extraction of the free base into benzene followed by distillation of the base yielded 1-methyl-3a-(m-methoxyphenyl)-1,2,3,3a,4,5,6,7-,7a,8-decahydroisoquinoline boiling in the range 145–79° C. at 0.1 mm/Hg. The corresponding picrate salt melted at about 161–2° C. after recrystallization from a aqueous ethanol. Overall yield through the sodium borohydride reduction procedure was about 90 percent.

Alternately, 1-methyl-3a-(m-methoxyphenyl)-1,2,3,3a,4,5,6,7-octahydroisoquinoline was reduced over platinum oxide with hydrogen to yield the corresponding decahydroisoquinoline. 66.7 g. of the octahydro compound were dissolved in 650 ml. of absolute ethanol. 5 g. of platinum oxide catalyst were added, and the hydrogenation mixture subjected to 60 psi of hydrogen. The yield of 1-methyl-3a-(m-methoxyphenyl)-1,2,3,3a,4,5,6,7,7a,8-decahydroisoquinoline synthesized by this procedure was about 96 percent. The compound was again isolated as the picrate salt.

The 1-methyl group was cleaved from the above decahydroisoquinoline by dissolving 8 g. of 1-methyl-3a-(m-methoxyphenyl)-1,2,3,3a,4,5,6,7,7a,8-decahydroisoquinoline in 64 ml. of methylene chloride and adding thereto a solution of 5.6 g. of phenyl chloroformate in 16 ml. of methylenechloride. The resulting mixture was refluxed for about 2 hours, and allowed to stand overnight. The solvents were then evaporated in vacuo. 100 ml. of 5 percent aqueous sodium hydroxide were added, and the resulting mixture stirred with warming for about 15 minutes. 1-Phenylcarboxy-3a-(m-methoxyphenyl)-1,2,3,3a,4,5,6,7,7a,8-decahydroisoquinoline formed in the above reaction, being insoluble in the basic layer, separated and was extracted into ether. The ether extract was separated and washed with water. The ether extract was in turn extracted with 250 ml. of 10 percent aqueous hydrochloric acid followed by 250 ml. of water to remove any unreacted N-methyldecahydroisoquinoline. The ether layer was separated, dried, and the ether removed by evaporation. The residue was refluxed for 66 hours in 240 ml. of anhydrous ethanol and 50 ml. of 50 percent aqueous potassium hydroxide. The volatile constituents were removed in vacuo and the resulting concentrate extracted with ether. The ether extract was separated and dried. Evaporation of the ether left a residue comprising 1-phenylcarboxy-3a-(m-methoxyphenyl)-1,2,3,3a,4,5,6,7,7a,8-decahydroisoquinoline which was dissolved in 250 ml. of 10 percent aqueous hydrochloric acid. The acid layer was washed with ether, and the ether wash was discarded. The aqueous layer was made strongly basic with 50 percent sodium hydroxide, and 3a-(m-methoxyphenyl)-1,2,3,3a,4,5,6,7,7a,8-decahydroisoquinoline thus formed was extracted into ether. The ether layer was separated, dried and the ether removed therefrom by evaporation. Distillation of the resulting residue yielded 5.5 g. of 3a-(m-methoxyphenyl)-1,2,3,3a,4,5,6,7,7a,8-decahydroisoquinoline boiling at about 148° C. at 0.2 mm/Hg.

3a-(m-methoxyphenyl)-1,2,3,3a,4,5,6,7,7a,8-decahydroisoquinoline was converted to the corresponding 3a-(m-hydroxyphenyl) derivative by treatment with 50 percent HBr in 50 percent aqueous acetic acid. In this procedure, 5.2 g. of freshly distilled 3a-(m-methoxyphenyl)-1,2,3,3a,4,5,6,7,7a,8-decahydroisoquinoline were dissolved in 40 ml. of 50 percent aqueous hydrobromic acid and 40 ml. of 50 percent aqueous acetic acid. The resulting mixture was refluxed for 18 hours. The reaction mixture was cooled, diluted with about 250 ml. of water and the pH thereof adjusted to about 10.4 with 50 percent aqueous sodium hydroxide. The reaction mixture was treated with a 3:1 n-butanol-benzene solvent system. 3a-(m-Hydroxyphenyl)-1,2,3,3a,4,5,6,7,7a,8-decahydroisoquinoline being insoluble in the alkaline layer passed into the organic layer. The organic layer was separated and dried, and the solvents removed therefrom by evaporation in vacuo. 5 g. of 3a-(m-Hydroxyphenyl)-1,2,3,3a,4,5,6,7,7a,8-decahydroisoquinoline were obtained which melted at about 212-214° C. with decomposition after recrystallization from dimethylformamide.

Analysis:Calc.: C, 76.67; H, 9.65; N, 6.39; Found: C, 76.88; H, 9.35; N, 6.24.

EXAMPLE 2

A mixture was prepared from 2.31 g. of 3a-(m-hydroxyphenyl)-1,2,3,3a,4,5,6,7a,8-decahydroisoquinoline, 1.22 g. of ethyliodide, 1.20 g. of sodium bicarbonate and 30 ml. of dimethylformamide. The reaction mixture was heated to refluxing temperatures for about one hour and then cooled. After the reaction mixture had cooled, it was diluted with ice water. 1-Ethyl-3a-(m-hydroxyphenyl)-1,2,3,3a,4,5,6,7,7a,8-decahydroisoquinoline formed in the above reaction being insoluble in water was extracted into ether. The ether extract was separated, dried and the ether removed by evaporation to dryness in vacuo. The residue was shown to be one-spot (fine) material on TLC. One gram of the residue was dissolved in 15 ml. of ethyl acetate. A solution of 0.5 g. of maleic acid was added thereto. The resulting mixture was refluxed and cooled after 2 ml. of ethanol had been added. The maleate salt precipitated and was collected by filtration. 1-Ethyl-3a-(m-hydroxyphenyl)-1,2,3,3a,4,5,6,7,7a,8-decahydroisoquinoline maleate thus prepared melted at about 138–140° C. after recrystallization from ethyl acetate.

Analysis:Calc. for $C_{21}H_{29}NO_5$: C, 67.18; H, 7.79; N, 3.73; Found: C, 66.92; H, 7.55; N, 3.57.

The above reaction can be carried out with 3a-(m-methoxyphenyl)-1,2,3,3a,4,5,6,7,7a,8-decahydroisoquinoline from the previous example to provide 1-ethyl-3a-(m-methoxyphenyl)-1,2,3,3a,4,5,6,7,7a,8-decahydroisoquinoline.

As previously stated, the compounds of this invention represented by Formula I above contain two asymmetric centers, at 3a and 7a. Thus the compounds can exist as four diastereoisomers occurring as two racemic pairs, commonly designated as the cis-dl and the trans-dl racemates. Any given racemic pair can be resolved into its optical antipodes by treatment of the racemate with an optically active acid as for example L(+)-mandelic acid or D(−)-mandelic acid.

In carrying out such a procedure, one-half mole of an optically-active mandelic acid in solution is added to a solution of a mole of, for example, trans-dl-1-ethyl-3a-(m-hydroxyphenyl)-1,2,3,3a,4,5,6,7,7a,8-decahydroisoquinoline. The salt of L(+)-mandelic acid and the trans-l(−)-decahydroisoquinoline isomer precipitates and is isolated. The free base is readily obtained from the salt by standard procedures.

EXAMPLE 3

Preparation of Salts

Salts of the free bases of this invention, other than the mandelate and maleate salts whose preparation is illustrated above, are prepared by dissolving the free base in ether and adding an equivalent of a suitable non-toxic acid, also in ether. The salts thus formed, as for example the sulfate and phosphate salts, are insoluble in ether and can be isolated by filtration. Alternatively, the amine base can be dissolved in ethanol and an equivalent of the acid added as an ethanolic solution. In this instance, since the salts thus formed are soluble in the reaction mixture, they are isolated by evaporation of the solvent in vacuo. Salts which can be formed by the above procedure include the hydrochloride, sulfate, hydrobromide, phosphate, hydrogen phosphate, dihydrogen phosphate, acetate, maleate, succinate, tartrate, citrate, benzoate, and p-toluene sulfonate salts of N-ethyl 3a-(m-hydroxyphenyl)-1,2,3,3a,4,5,6,7,7a,8-decahydroisoquinoline of this invention and the corresponding m-alkoxy and m-acyloxy derivatives.

As previously stated, the compounds of this invention have both opiate agonist and opiate antagonist properties. While the compounds are capable of producing analgesia in mammals, the added characteristic of being simultaneously an opiate-antagonist greatly decreases the addiction liability of the particular drug. It might be said that the opiate-antagonist activity of the compounds of this invention acts as a built-in safety device tending to mitigate any physical dependence-inducing (addictive) properties of the drug caused by its opiate-like analgesic action. Thus, the free bases and salts of this invention can be used to produce opiate-like analgesia with minimal physical dependence liability.

The compounds of this invention demonstrate their analgesic activity in the mouse-writhing test and in the rat tail jerk assay, both standard pharmacological assays for analgesic action. For example, 1-ethyl-3a-(m-hydroxyphenyl)-1,2,3,3a, 4,5,6,7,7a,8-decahydroisoquinoline inhibits writhing induced in mice by the intraperitoneal injection of acetic acid. With the test compound being injected subcutaneously, the following results were obtained: a 100 mg./kg. dose gave 83 percent inhibition of writhing; a 20 mg./kg. dose, 94 percent inhibition; and a 2 mg./kg. dose, 47 percent inhibition (all readings made at one-half hour). Oral dosages gave the following results: 100 mg./kg., 76 percent inhibition; and 50 mg./kg., 56 percent inhibition. Naloxone partially prevented the inhibitory action of the compound at the 100 mg./kg. level, thus demonstrating that the compound is an opiate-agonist. In the above tests, the compound was administered as a suspension. In the rat tail jerk assay, the same compound increased the reaction time at dose levels from 20 to 80 mg./kg. when administered by the subcutaneous route, thus demonstrating analgesic action. Effects at these dose levels were statistically significant; thus, the minimum effective dose as an analgesic is about 20 mg./kg. by the subcuanteous route.

In opiate-antagonist studies, the compound, when given to rats orally 60 minutes prior to testing at a dose level of 20 mg./kg. decreased the expected increase in reaction time produced by morphine administered at a dose level of 5 mg./kg. subcutaneously 10 minutes prior to test. At a dose level of 50 mg./kg. orally, the compound was able to essentially completely block the increased reaction time produced by administration of 5 mg./kg. subcutaneously of morphine 10 minutes prior to test. The minimum opiate-antagonist dose is in the range 10–20 mg./kg. subcutaneously and is about 20 mg./kg. orally. By contrast, 1-methyl-3a-(m-hydroxyphenyl)-1,2,3,3a,4,5,6,7,7a,8-decahydroisoquinoline is substantially a pure agonist without opiate-antagonist properties.

The compounds of this invention can be employed to produce analgesia in mammals by administration via either the parenteral or oral route. For oral dosage, a suitable quantity of a pharmaceutically-acceptable salt of a base according to Formula I, formed with a non-toxic acid, is mixed with starch or other excipient, and the mixture placed in telescoping gelatin capsules each containing an analgesic dose. Similarly, the salt can be mixed with starch, a binder, a lubricant, and the mixture compressed into tablets each containing a standard analgesic dose. The tablets may be scored if lower or divided dosages are to be used. With parenteral administration, the intramuscular or subcutaneous routes are preferred. For this purpose, aqueous solutions or suspensions are employed using a pharmaceutically-acceptable salt of the amine base of formula 1. In general, modes of administration and pharmaceutical forms found useful in the past for morphine, codeine, methadon, meperidine and other opiate-like analgesics can be adopted by those skilled in the art for the compounds of this invention.

We claim
1. A compound of the formula

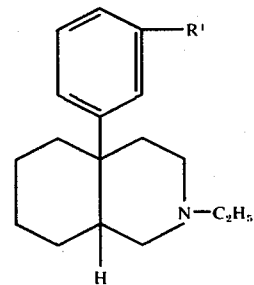

wherein
R[1] is O-alk or OH; and
alk is (C$_1$–C$_3$) alkyl.

2. A compound according to claim 1, said compound being 1-ethyl-3a-(m-hydroxyphenyl)-1,2,3,3a,4,5,6,7,7a,8-decahydroisoquinoline.

3. A compound according to claim 1, said compound being 1-ethyl-3a-(m-methoxyphenyl)-1,2,3,3a,4,5,6,7,7a,8-decahydroisoquinoline.

4. A pharmaceutically-acceptable acid addition salt of a compound of claim 1, formed with a non-toxic acid.

5. A trans-dl racemate of a compound according to claim 1.

6. A trans-dl racemate of a compound according to claim 1 in which R' is OH.

* * * * *